United States Patent
Li et al.

(10) Patent No.: US 10,311,603 B2
(45) Date of Patent: Jun. 4, 2019

(54) CORRECTING POSITRON EMISSION TOMOGRAPHY IMAGE ATTENUATION

(71) Applicant: Shenyang Neusoft Medical Systems Co., Ltd., Shenyang (CN)

(72) Inventors: Yunda Li, Shenyang (CN); Yue Liu, Shenyang (CN)

(73) Assignee: SHENYANG NEUSOFT MEDICAL SYSTEMS CO., LTD., Shenyang, Liaoning (CN)

(*) Notice: Subject to any disclaimer, the term of this patent is extended or adjusted under 35 U.S.C. 154(b) by 0 days.

(21) Appl. No.: 15/809,939

(22) Filed: Nov. 10, 2017

(65) Prior Publication Data
US 2018/0137656 A1  May 17, 2018

(30) Foreign Application Priority Data

Nov. 11, 2016 (CN) .......................... 2016 1 1048076

(51) Int. Cl.
| | |
|---|---|
| G06K 9/62 | (2006.01) |
| G06T 11/00 | (2006.01) |
| G06T 7/11 | (2017.01) |
| A61B 5/055 | (2006.01) |
| A61B 6/03 | (2006.01) |
| A61B 6/00 | (2006.01) |
| G06T 5/50 | (2006.01) |
| G06T 7/30 | (2017.01) |

(52) U.S. Cl.
CPC .......... *G06T 11/005* (2013.01); *A61B 5/055* (2013.01); *A61B 6/037* (2013.01); *A61B 6/5235* (2013.01); *G06K 9/6202* (2013.01); *G06T 5/50* (2013.01); *G06T 7/11* (2017.01); *G06T 7/30* (2017.01); *G06T 11/003* (2013.01); *A61B 6/032* (2013.01); *A61B 6/5205* (2013.01); *A61B 2576/00* (2013.01); *G06T 2207/10081* (2013.01); *G06T 2207/10084* (2013.01); *G06T 2207/10088* (2013.01); *G06T 2207/10104* (2013.01); *G06T 2207/20128* (2013.01)

(58) Field of Classification Search
None
See application file for complete search history.

(56) References Cited

U.S. PATENT DOCUMENTS

| | | | | |
|---|---|---|---|---|
| 7,280,710 B1* | 10/2007 | Castro-Pareja | ........... | G06T 7/35 382/154 |
| 7,899,231 B2* | 3/2011 | Novak | ...................... | G06T 5/50 378/4 |

(Continued)

*Primary Examiner* — Tahmina N Ansari
(74) *Attorney, Agent, or Firm* — Ladas & Parry, LLP (57) ABSTRACT

Method of correcting PET image attenuation and PET/MRI devices are provided. In one aspect, an MRI image of a subject is segmented to obtain respective MRI sub-images corresponding to attenuation units of the subject, respective pseudo CT sub-images corresponding to the MRI sub-images are obtained based on an MRI-CT atlas, the respective pseudo CT sub-images corresponding to the MRI sub-images are spliced to obtain a pseudo CT image corresponding to the MRI image, and attenuation correction is performed for a PET image of the subject according to the pseudo CT image, wherein the PET image and the MRI image are obtained through a same scan process for the subject.

10 Claims, 6 Drawing Sheets

(56) References Cited

U.S. PATENT DOCUMENTS

| | | | |
|---|---|---|---|
| 2006/0171578 A1* | 8/2006 | Novak | G06T 5/50 382/131 |
| 2011/0007959 A1* | 1/2011 | Schulz | A61B 5/055 382/131 |
| 2018/0137656 A1* | 5/2018 | Li | G06T 11/003 |

* cited by examiner

CORRECTING POSITRON EMISSION TOMOGRAPHY IMAGE ATTENUATION

CROSS REFERENCE TO RELATED APPLICATIONS

This application claims priority to Chinese Patent Application No. 201611048076.7 entitled "Method and Apparatus for Correcting PET Image Attenuation" filed on Nov. 11, 2016, the entire content of which is incorporated herein by reference.

TECHNICAL FIELD

The present disclosure relates to a medical image processing technologies, and prefers to correcting PET image attenuation.

BACKGROUND

Multimodal medical images can be obtained by scanning a subject through a multimodal imaging device, which include at least two types of medical images for the same subject, such as PET/CT images, PET/MRI images and the like. For example, a PET/MRI device is a multimodal imaging device, which can obtain a PET image and an MRI image for the same subject.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analysers. Currently, NMS products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

DETAILED DESCRIPTION

Example embodiments will be described in detail herein with the examples thereof expressed in the drawings. When the following descriptions involve the drawings, like numerals in different drawings represent like or similar elements unless stated otherwise. The implementations described in the following example embodiments do not represent all implementations consistent with the present disclosure. On the contrary, they are examples of an apparatus and a method consistent with some aspects of the present disclosure as detailed in the appended claims.

Compared with a mono-modal medical image (e.g., single PET, MRI or CT), multimodal medical images (e.g., those utilizing more than one type of image, such as utilizing two or more of PET, MRI, and other types of medical imaging) can provide more information about tissue structures and other details, and at least two types of image information about the multimodal medical images can be comprehensively used to improve reconstruction image quality. For example, the PET/MRI device reconstructs a PET image by using information of an MRI image to acquire better quality of the reconstructed PET image.

When a PET image is reconstructed, accuracy of the reconstructed PET image is directly affected by attenuation of γ-rays for a tissue structure of a subject based on a PET imaging mechanism. Thus, attenuation correction is desired to be performed for a PET image.

Multimodal medical images may include at least two types of medical images obtained by scanning a same subject. For example, a PET image and an MRI image of a same subject can be obtained by using a PET/MRI device. The MRI image provides information about proton density and relaxation time which are not directly associated with attenuation capability of a tissue for γ-rays on the subject, thus, the MRI image cannot be directly used to perform attenuation correction for the PET image. However, the MRI image may be converted into a pseudo CT image, and attenuation correction for the PET image may be performed based on the pseudo CT image. The pseudo CT image herein is a converted image which is similar to a CT image obtained through an actual CT scan (for example, on image intensity and image shape), rather than an image obtained through the CT scan.

An MRI-CT atlas can be used when the MRI image is converted into the pseudo CT image. The MRI-CT atlas can be a sample set of MRI images and CT images, where each MRI image corresponds to a CT image, and a corresponding pair of an MRI image and a CT image can be obtained by scanning the same part of the same subject. In the present discussion, an MRI-CT atlas obtained for one subject can then be applied to a different subject or the same subject.

In an example of generating the MRI-CT atlas, a subject j1 can be divided into a plurality of body parts, such as a body part B1, a body part B2 and the like. A human body can be taken as an example of the subject, body parts can be organs or other parts of the human body, such as lungs, a skeleton, soft tissue fat and the like or portions thereof. A CT image and a MRI image for the subject J1 can be obtained in a same scanning condition (e.g., a same scanning body position/orientation and a same body condition and so on), and respective image parts corresponding to the same body part of the same subject in the MRI image and the PET image can be obtained, such as a CT image part and an MRI image part corresponding to the lungs, a CT image part and an MRI image part corresponding to the skeleton and the like.

Figure 1:
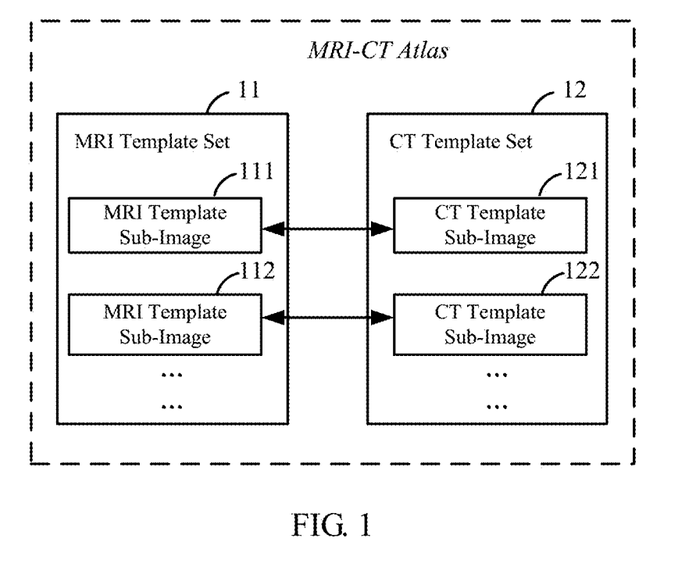
FIG. 1 is a schematic diagram illustrating an MRI-CT atlas according to an example of the present disclosure.

In an example of FIG. 1, the MRI-CT atlas includes an MRI template set 11 and a CT template set 12. The CT image part corresponding to the lungs can be put into the CT template set 12, which can be referred to as a CT template sub-image 121. In one embodiment, an MRI image part corresponding to the lungs can be put into MRI template set 11, which can be referred to as MRI template sub-image 111, where the MRI template sub-image 111 and the CT template sub-image 121 correspond to the same body part (e.g. lungs) of the same subject, as described above. Similarly, in FIG. 1, in another embodiment, an MRI template sub-image 112 and a CT template sub-image 122 can correspond to the skeleton. In additional embodiments, the MRI template set 11 and the CT template set 12 may further include a plurality of template sub-images corresponding to another part of the subject or parts of the subject, which can be any anatomical part or collection of parts, the listing of which is not enumerated here but can be found in numerous anatomy textbooks, the listing of parts is included herein by reference.

In the MRI-CT atlas above, a pair of a MRI template sub-image and a CT template sub-image correspond to the same subject. However, the atlas can include images for a plurality of subjects. For example, the atlas includes the MRI template sub-image and the CT template sub-image corresponding to the lungs of the subject J1, and further includes a MRI template sub-image and a CT template sub-image corresponding to lungs of the subject J2. The atlas can also include images of subject J1 for some body parts and images of subject J2 for different body parts.

Figure 2:
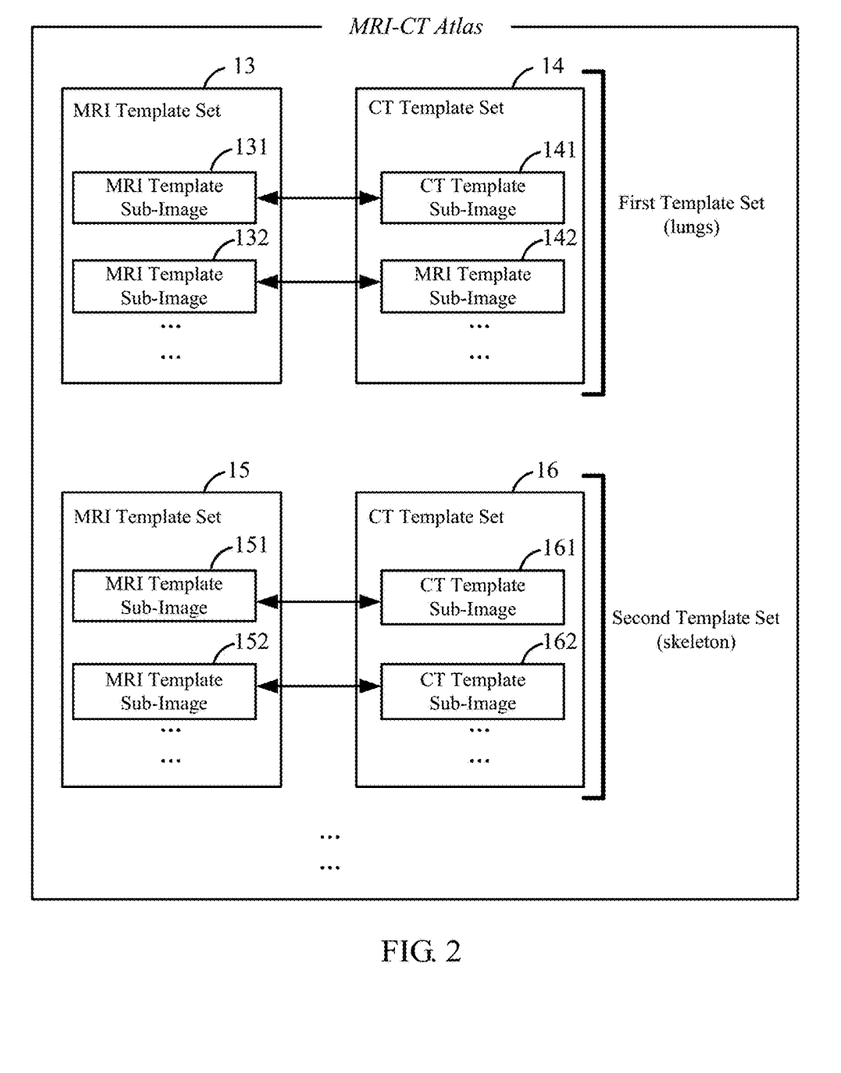
FIG. 2 is a schematic diagram illustrating an MRI-CT atlas according to another example of the present disclosure.

In FIG. 2, respective template sub-images corresponding to body parts can be separately stored in the MRI-CT atlas. For example, images of lungs can be stored together, which can be referred to as a first template set. The first template set includes an MRI template set 13 and a CT template set 14 which can include respective images of the same region (e.g. lungs) of subjects. For example, an MRI template sub-image 131 and a CT template sub-image 141 can be images of lungs of the subject J1, and an MRI template sub-image 132 and a CT template sub-image 142 can be images of lungs of the subject J2. A second template set in FIG. 2 can include images of the skeleton, which can include an MRI template set 15 and a CT template set 16. An MRI template sub-image 151 and a CT template sub-image 161 can correspond to skeleton of the subject J1, and an MRI template sub-image 152 and a CT template sub-image 162 can correspond to skeleton of the subject J2.

A process that an MRI image obtained by a PET/MRI device can be converted into a pseudo CT image based on the MRI-CT atlas is described below.

Figure 3:
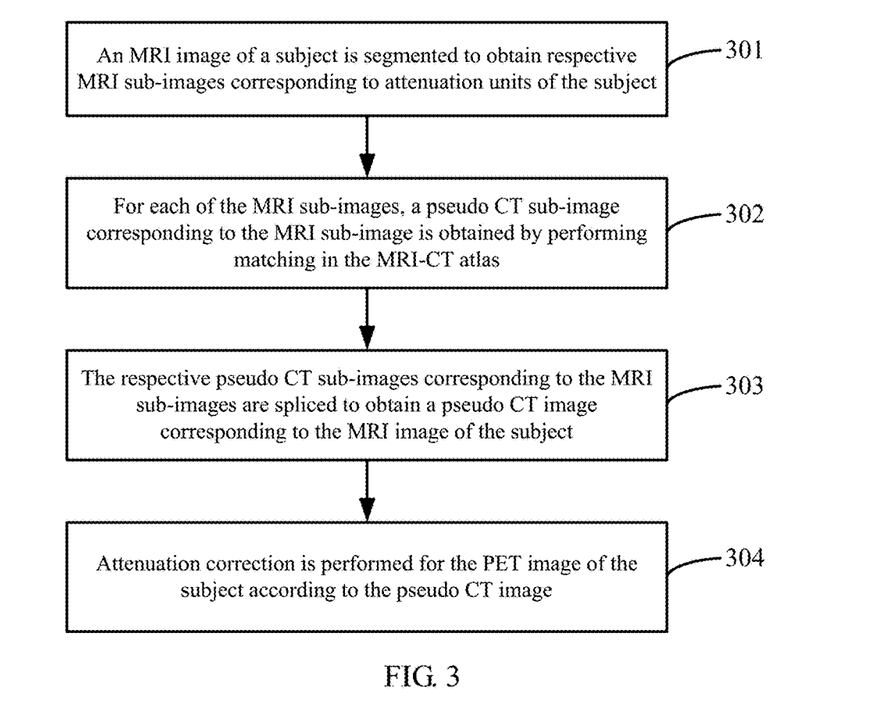
FIG. 3 is a flowchart illustrating a process of correcting PET image attenuation according to an example of the present disclosure.

FIG. 3 is a flowchart illustrating a method of converting an MRI image and performing PET image attenuation correction according to an embodiment of the present disclosure. The method includes procedures as follows.

At block 301, an MRI image of a subject can be segmented to obtain respective MRI sub-images corresponding to attenuation units of the subject.

In the block, the MRI image can be segmented according to the attenuation units. Different attenuation units have different attenuation properties. For example, when the subject is a human body, an attenuation unit may be an organ tissue of the human body, such as a skeleton, soft tissue, lungs, fat and the like.

For example, respective images for the organ tissues can be extracted from the MRI image by a segmentation method, such as a threshold method or a region growing method. In the example, the image for an organ tissue can be referred to as an MRI sub-image. For example, the lungs can correspond to a MRI sub-image, and the skeleton can correspond to another MRI sub-image.

At block 302, for each of the MRI sub-images, a pseudo CT sub-image corresponding to the MRI sub-image can be obtained by performing matching in the MRI-CT atlas.

For each of the MRI sub-images obtained in block 301, the pseudo CT sub-image corresponding to the MRI sub-image can be obtained. In the process above, the matching can be performed in the atlas based on shape and intensity of the MRI sub-image.

Figure 4:
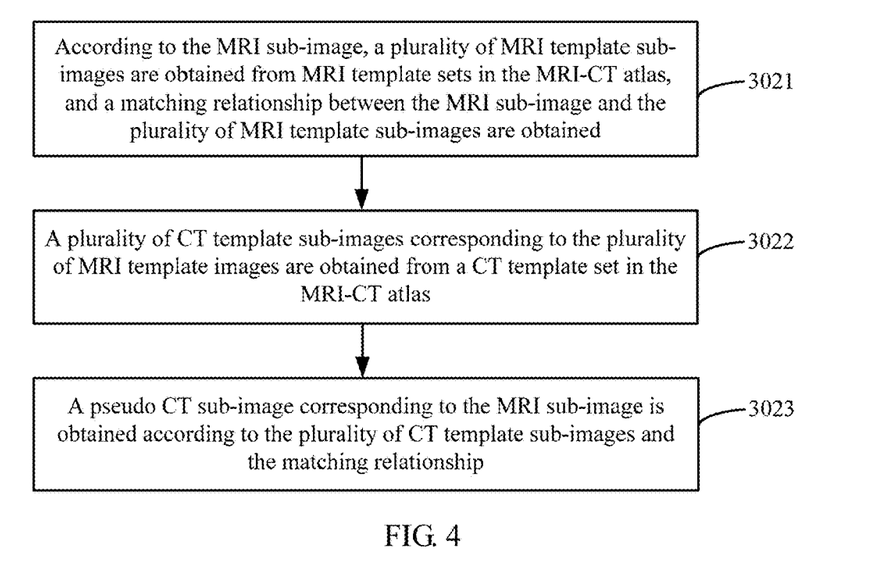
FIG. 4 is a flowchart illustrating a process of performing image conversion based on an atlas according to an example of the present disclosure.

FIG. 4 is a flowchart illustrating a process of performing image conversion based on an atlas according to an example of the present disclosure. In FIG. 4, an MRI sub-image can be taken as an example of image conversion to describe how a pseudo CT sub-image corresponding to the MRI sub-image can be obtained according to the atlas, and image conversion for another MRI sub-image can be same as that in the process. In FIG. 4, the process includes procedures as follows.

At block 3021, according to the MRI sub-image, a plurality of MRI template sub-images can be obtained from MRI template sets in the MRI-CT atlas, and a matching relationship between the MRI sub-image and the plurality of MRI template sub-images can be obtained, where the matching relationship can include applying weighting coefficients to the MRI template sub-images image intensity and/or image shape in a way that a weight sum of the plurality of MRI template sub-images can be matched with the MRI sub-image where the weight sum of the plurality of MRI template sub-images presents a better fit to the MRI sub-images than the unweighted template sub-images. In some embodiments, the match will be exact and in some embodiments the match will not be exact, but can have a predetermined degree of closeness.

In the example, a plurality of MRI template sub-images corresponding to the MRI sub-image can be obtained from the atlas. The MRI sub-image of the lungs can be taken as an example. In FIG. 2, the MRI template sub-images can be searched for from the MRI template set 13 in the first template set corresponding to the lungs. The MRI template set 13 includes respective lungs images of human bodies. For example, the MRI template sub-image 131 and the MRI template sub-image 132 can be images of the lungs obtained by respectively performing MRI scan for two persons, Mr. Wang and Mr. Zhang. In an example, the obtained MRI template sub-images can be a part or all of images in the first template set.

A matching relationship between the MRI sub-image and the MRI template sub-images can be obtained in this block. The matching relationship includes respective weighting coefficients for the MRI template sub-images based on image intensity and image shape in a way that a weight sum of the plurality of MRI template sub-images can be matched with the MRI sub-image. For example, it is assumed that K MRI template sub-images correspond to the MRI sub-image, where each of the MRI template sub-images can be different from the MRI sub-image on shape and intensity, the matching relationship can be obtained in this block. The matching relationship can be a transformation relationship, which indicates that how shapes and intensities of the K MRI template sub-images above can be transformed (e.g., a shape transformation function) to obtain a transformation result a shape and an intensity of which can be the same as or sufficiently close to that of the MRI sub-image.

In an example, the transformation relationship between the plurality of MRI template sub-images and the MRI sub-image is described below.

The MRI sub-image can be expressed by $M_{patient}^i$, and the MRI template sub-image can be expressed by $M_{template}^{ik}$.

It is assumed that the number of the obtained MRI template sub-images is K. The MRI sub-image and the MRI template sub-images satisfies a relationship as follows:

$$M_{patient}^i = \sum_{k=1}^{K} t_k T_{ik}(M_{template}^{ik}) \quad (1)$$

In the formula (1), parameter $t_k$ represents an intensity weight factor of each of the K MRI template sub-images. For example, the $t_k$ is $e^{-f(k)}$ where f(k) is the absolute value of the difference in intensity between the MRI sub-image k and the corresponding MRI template sub-image. A perfect match would result in $$\sum_{k=1}^{K} t_k = 1.$$

Parameter $T_k$ represents a shape transformation function through which the shape of the MRI template sub-image can be transformed to be matched with the shape of the MRI sub-image, which can be referred to as a shape factor. For example, the parameter can be determined according to an elastic registration method or the like.

According to formula (1), when the K MRI template sub-images can be selected from the MRI template set 13, respective weight sums for intensity and sharpness can be acquired according to the relationship of the formula (1). When the weight sum of shapes of the K MRI template sub-images are same as (or sufficiently close to, such as by a predetermined degree of closeness as measured by $\Sigma_{k=1}^{K} t_k$ or $\Sigma_{k=1}^{K} t_{ik}$ closeness to 1, such as within 1%, 2%, 3%, 4%, 5%, 6%, 7%, 8%, 9% or 10%) those of the MRI sub-image and the weight sum of intensities of the K MRI template sub-images are the same as (or sufficiently close to, such as by a predetermined degree of closeness as measured by $\Sigma_{k=1}^{K} t_k$ or $\Sigma_{k=1}^{K} t_{ik}$ closeness to 1, such as within 1%, 2%, 3%, 4%, 5%, 6%, 7%, 8%, 9% or 10%) those of the MRI sub-image, it can be regarded that the K MRI template sub-images are matched with the MRI sub-image. In the example, the relationship in the formula (1) can be the matching relationship between the MRI sub-image and the plurality of MRI template sub-images.

At block 3022, a plurality of CT template sub-images corresponding to the plurality of MRI template images can be obtained from a CT template set in the MRI-CT atlas.

For example, in FIG. 2, after the K MRI template sub-images in the MRI template set can be obtained in block 3021, the plurality of CT template sub-images corresponding to the plurality of MRI template images can be directly obtained according to correspondences. For example, the CT template sub-image 141 corresponds to the MRI template sub-image 131, and the CT template sub-image 142 corresponds to the MRI template sub-image 132.

At block 3023, a pseudo CT sub-image corresponding to the MRI sub-image can be obtained according to the plurality of CT template sub-images and the matching relationship.

$$C_{patient}^i = \sum_{k=1}^{K} t_k T_{ik}(C_{template}^{ik}) \quad (2)$$

In the formula (2), $C_{template}^{ik}$ represents a CT template sub-image, $C_{patient}^i$ represents the pseudo CT sub-image, the parameters $t_k$ and $T_{ik}$ can be same as those in the formula (1), values of the parameters $t_k$ and $T_{ik}$ in the formula (2) can be equal to values of corresponding parameters obtained in block 3021. In the formula (2), it can be indicated that the pseudo CT sub-image can be acquired by performing transformation for the K CT template sub-images obtained in block 3022 according to the matching relationship in the formula (2).

At block 303, the respective pseudo CT sub-images corresponding to the MRI sub-images can be spliced to obtain a pseudo CT image corresponding to the MRI image of the subject.

For example, as described above, $M_{patient}^i$ represents an MRI sub-image. That is, the MRI image of the subject can be segmented into I MRI sub-images, and a complete MRI image $M_{patient}$ can be acquired by performing combination for the I MRI sub-images.

$$M_{patient} = \sum_{i=1}^{I} M_{patient}^i \quad (3)$$

After respective pseudo CT sub-images corresponding to the MRI sub-images can be acquired, a complete pseudo CT image $C_{patient}$ can be acquired by performing combination for the I pseudo CT sub-images according to formula (4) below:

$$C_{patient} = \sum_{i=1}^{I} C_{patient}^i \quad (4)$$

At block 304, attenuation correction can be performed for the PET image of the subject according to the pseudo CT image.

For example, an attenuation correction factor can be obtained according to the pseudo CT image, and correction can be performed for chordal graph data for the PET projection obtained by the device through scan. So far, the attenuation correction in a PET/MRI system can be completed.

In the method example, the MRI image can be segmented based on attenuation units such as organ tissues in a way an error caused by a same segment containing a plurality of attenuation units can be avoided. Further, when matching is performed based on the atlas, image shape and image intensity can be used for performing matching in a way that the matching result can be more accurate, the obtained pseudo CT sub-images can be closer to images obtained through actual CT scan, better performance for the attenuation correction can be achieved, and the quality of PET image attenuation correction through the MRI image can be improved.

Figure 5:
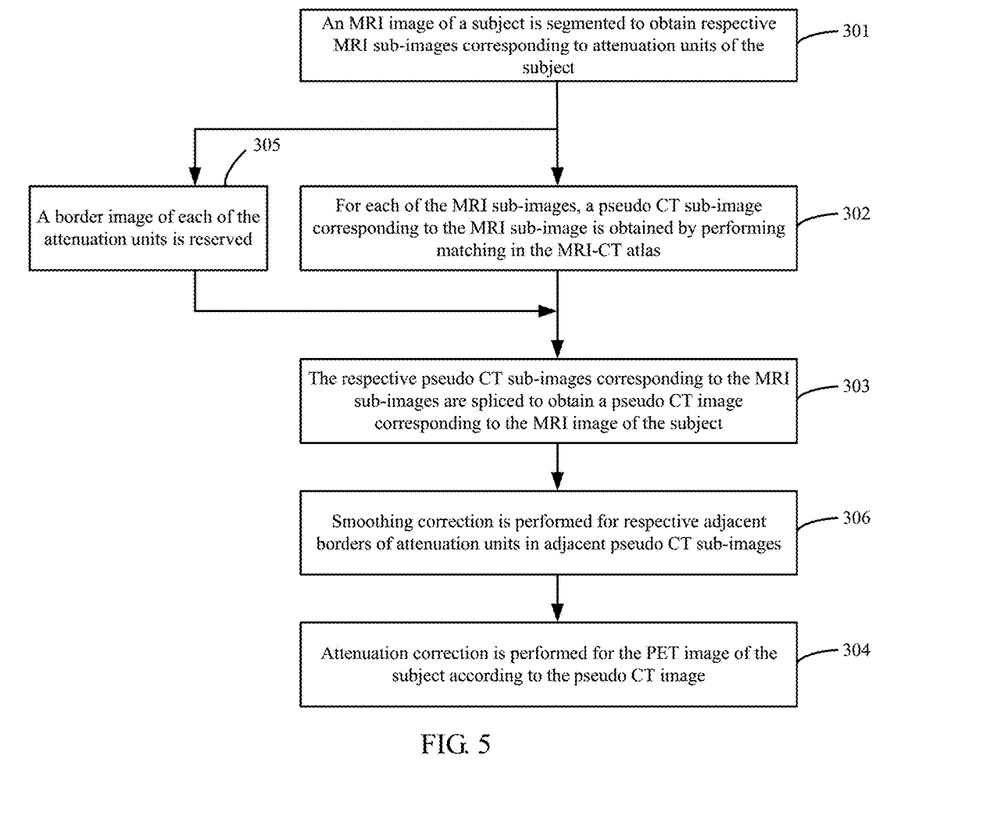
FIG. 5 is a flowchart illustrating a process of correcting PET image attenuation according to another example of the present disclosure.

In another example in FIG. 5, the MRI sub-images can be obtained through segmentation in block 301, and a border image of each of the attenuation units can be reserved in block 305, so as to achieve the pseudo CT image with high accuracy.

For example, borders in the MRI sub-images can be extracted according to the MRI sub-images. When the borders in the MRI sub-images can be extracted, internal textures of organ tissues can be extracted as well. According to the segmented images, the borders of the organs can be reserved, and internal contour lines can be removed. The obtained border images can provide "block graphs" for the CT sub-images subsequently obtained in a way that the CT sub-images can be accurately placed into corresponding locations.

The respective border images of the attenuation units corresponding to the MRI sub-images can be used to splice the CT sub-images in block 303. The border images in which the borders of the organ tissues can be reserved can be used as reference, and the CT sub-images can be placed into corresponding locations in the border images. In an example, respective pseudo CT sub-images can be placed into border images of the attenuation units to obtain a complete pseudo CT image with high splicing accuracy.

Further, in block 306, smoothing correction can be performed for respective adjacent borders of attenuation units in adjacent pseudo CT sub-images. For example, adjacent borders between organ tissues can have sharp changes when the obtained pseudo CT sub-images are directly spliced to an image, such as blocks in the image, which make the image look unnatural. To make transitions between organ tissues more natural and complete, values corresponding to the adjacent borders of the attenuation units in the two pseudo CT sub-images being joined can be weighted according to a method such as an averaging method or an exponential weighting method.

Further, in another example, the border images are not reserved, and the CT sub-images can be directly spliced to the pseudo CT image. In this case, the adjacent borders of the attenuation units in the adjacent CT sub-images can be smoothed. For example, a location on the adjacent borders can be acquired by determining whether a difference between values on two sides of a pixel point is more than a threshold value (if yes, the pixel is on the borders), and the smoothing processing can be performed for the adjacent borders.

According to methods of correcting PET image attenuation in the example, transitions between organ tissues in the pseudo CT image can be smoother and more natural in a way that the pseudo CT image can be closer to an image obtained through actual CT scan, an error between an attenuation correction factor obtained according to the pseudo CT image and an attenuation correction factor obtained from an actual CT scan can be small, thereby improving attenuation correction quality.

Figure 6:
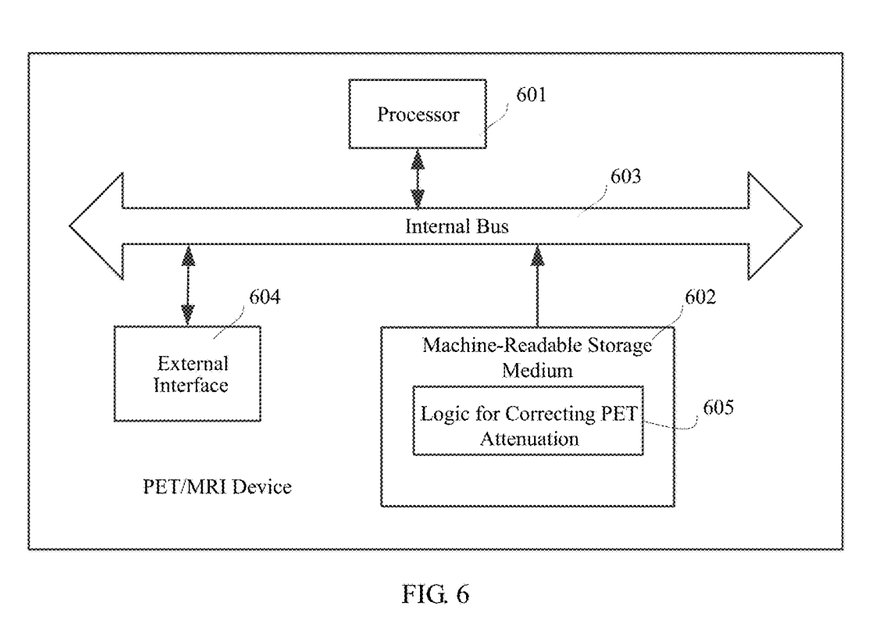
FIG. 6 is a schematic diagram illustrating a structure of a PET/MRI device according to an example of the present disclosure.

FIG. 6 schematically illustrates a hardware structure diagram of a PET/MRI device according to an example of the present disclosure. The PET/MRI device can include a processor 601 and a machine-readable storage medium 602 storing machine executable instructions. The processor 601 may communicate with the machine-readable storage medium 602 via an internal bus 603, and execute the method described above by reading and executing the machine executable instructions corresponding to control logic in the machine-readable storage medium 602. The PET device can further include an external interface 604 to communicate with another device or component. Further, the machine-readable storage medium 602 can store a logic 605 for correcting PET image attenuation.

Figure 7:
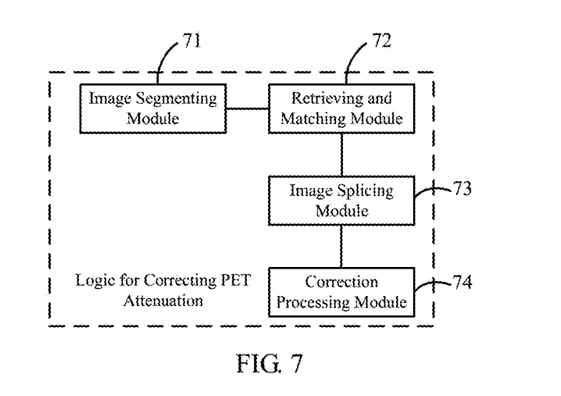
FIG. 7 is a schematic diagram illustrating logic for correcting PET image attenuation according to an example of the present disclosure.

As shown in FIG. 7, the logic 605 can include an image segmenting module 71, a retrieving and matching module 72, an image splicing module 73 and a correction processing module 74.

The image segmenting module 71 can be configured to segment an MRI image of a subject to obtain respective MRI sub-images corresponding to attenuation units of the subject.

The retrieving and matching module 72 can be configured to obtain respective pseudo CT sub-images corresponding to the MRI sub-images based on an MRI-CT atlas.

The image splicing module 73 can be configured to splice the respective pseudo CT sub-images corresponding to the MRI sub-images to obtain a pseudo CT image corresponding to the MRI image.

The correction processing module 74 can be configured to perform attenuation correction for a PET image of the subject according to the pseudo CT image, wherein the PET image and the MRI image can be obtained through a same scan process for the subject.

Figure 8:
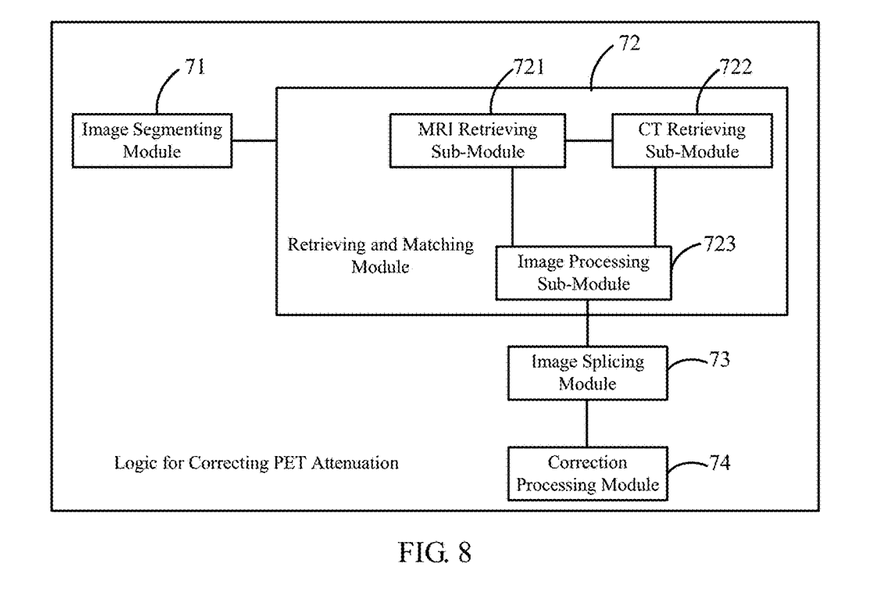
FIG. 8 is a schematic diagram illustrating logic for correcting PET image attenuation according to another example of the present disclosure.

In an example, as shown in FIG. 8, the retrieving and matching module 72 may also include sub-modules as follows.

An MRI retrieving sub-module 721 can be configured to obtain, for each of the MRI sub-images, a plurality of MRI template sub-images associated with the attenuation unit corresponding to the MRI sub-image from an MRI template set in the MRI-CT atlas, and obtain a matching relationship between the plurality of MRI template sub-images and the MRI sub-image, wherein the matching relationship comprises respective weighting coefficients for the MRI template sub-images based on image intensity and image shape in a way that a weight sum of the plurality of MRI template sub-images can be matched with the MRI sub-image.

A CT retrieving sub-module 722 can be configured to obtain a plurality of CT template sub-images corresponding to the plurality of MRI template sub-images from a CT template set in the MRI-CT atlas.

An image processing sub-module 723 can be configured to obtain the pseudo CT sub-image corresponding to the MRI sub-image according to the plurality of CT template sub-images and the matching relationship.

In an example, the image splicing module 73 can be configured to place the respective pseudo CT sub-images into border images for the attenuation units corresponding to the respective pseudo CT sub-images.

In an example, the image processing sub-module 723 can be configured to perform smoothing correction for respective adjacent borders of attenuation units in adjacent pseudo CT sub-images.

In an example, an attenuation unit can be an organ tissue of the subject.

In different examples, the machine readable storage medium 602 can include: a Random Access Memory (RAM), a volatile memory, a non-volatile memory, a flash memory, a storage drive (e.g. hard disk drive), a solid state hard disk, any type of storage disk (e.g., optical disk, Digital Video Disk (DVD)), or a similar storage medium, or a combination thereof.

The foregoing disclosure is merely illustrative of preferred embodiments of the disclosure and is not intended to limit the present disclosure, and any modifications, equivalent substitutions, adaptations thereof made without departing from the spirit and scope of the present disclosure shall be encompassed in the claimed scope of the appended claims.

The invention claimed is:

1. A method of correcting Positron Emission Tomography (PET) image attenuation, comprising:
   segmenting an MRI image of a subject to obtain respective MRI sub-images corresponding to attenuation units of the subject;
   for each MRI sub-image, obtaining pseudo CT sub-images corresponding to the MRI sub-images based on an MRI-CT atlas, wherein,
      the pseudo CT sub-image is obtained by selecting a plurality of CT template sub-images present in the MRI-CT atlas that corresponds to a plurality of MRI template sub-images in the MRI-CT atlas matched to the MRI sub-image, and
      the plurality of MRI template sub-images is matched to the MRI sub-image by a matching relationship comprising shape factors and intensity weight factors;
   splicing the respective pseudo CT sub-images to obtain a pseudo CT image; and
   performing attenuation correction for a PET image of the subject according to the pseudo CT image, wherein the PET image and the MRI image are obtained through a same scan process for the subject.

2. The method of claim 1, wherein for each MRI sub-image obtaining the pseudo CT sub-images corresponding to the MRI sub-images based on the MRI-CT atlas comprises:
   obtaining the plurality of MRI template sub-images associated with the attenuation unit corresponding to the MRI sub-image from an MRI template set in the MRI-CT atlas;
   obtaining the matching relationship between the plurality of MRI template sub-images and the MRI sub-image, wherein
      the matching relationship comprises respective weighting coefficients for the MRI template sub-images based on image intensity and image shape such that a weight sum of the plurality of MRI template sub-images is matched with the MRI sub-image; and
      the matching relationship is calculated with formula (1):

$$M_{patient}^{i} = \sum_{k=1}^{K} t_k T_{ik} (M_{template}^{ik}), \quad (1)$$

wherein
   $t_k$ represents the intensity weight factor of the k-th MRI template sub-image,
   $T_{ik}$ represents the shape factor of the k-th MRI template sub-image,
   $M_{patient}^{i}$ represents the MRI sub-image i,
   $M_{template}^{ik}$ template represents the k-th MRI template sub-image corresponding to the MRI sub-image i, and
   K represents a number of the plurality of MRI template sub-image;
   obtaining the plurality of CT template sub-images corresponding to the plurality of MRI template sub-images from a CT template set in the MRI-CT atlas; and
   obtaining the pseudo CT sub-image corresponding to the MRI sub-image according to the plurality of CT template sub-images and the matching relationship.

3. The method of claim 1, wherein splicing the respective pseudo CT sub-images comprises:
   placing the respective pseudo CT sub-images into border images for the attenuation units corresponding to the respective pseudo CT sub-images.

4. The method of claim 1, further comprising:
   performing smoothing correction for respective adjacent borders of attenuation units in adjacent pseudo CT sub-images.

5. The method of claim 1, wherein the attenuation unit is an organ tissue of the subject.

6. A PET/MRI device, comprising:
   a processor, and
   a non-transitory machine-readable storage medium storing machine executable instructions which are executable by the processor to:
   segment an MRI image of a subject to obtain respective MRI sub-images corresponding to attenuation units of the subject;
   for each MRI sub-image, obtain a pseudo CT sub-images corresponding to the MRI sub-images based on an MRI-CT atlas, wherein;
      the pseudo CT sub-image is obtained by selecting a plurality of CT template sub-images present in the MRI-CT atlas that corresponds to a plurality of MRI template sub-images in the MRI-CT atlas matched to the MRI sub-image, and
      the plurality of MRI template sub-images is matched to the MRI sub-image by a matching relationship comprising shape factors and intensity weight factors;
   splice the respective pseudo CT sub-images to obtain a pseudo CT image; and
   perform attenuation correction for a PET image of the subject according to the pseudo CT image, wherein the PET image and the MRI image are obtained through a same scan process for the subject.

7. The device of claim 6, wherein the processor is caused by the machine-executable instructions to:
   obtain, for each of the MRI sub-images, the plurality of MRI template sub-images associated with the attenuation unit corresponding to the MRI sub-image from an MRI template set in the MRI-CT atlas;
   obtain the matching relationship between the plurality of MRI template sub-images and the MRI sub-image, wherein
      the matching relationship comprises respective weighting coefficients for the MRI template sub-images based on image intensity and image shape in a way that a weight sum of the plurality of MRI template sub-images is matched with the MRI sub-image; and
      the matching relationship is calculated with formula (1):

$$M_{patient}^{i} = \sum_{k=1}^{K} t_k T_{ik} (M_{template}^{ik}), \quad (1)$$

wherein
   $t_k$ represents the intensity weight factor of the k-th MRI template sub-image,
   $T_{ik}$ represents the shape factor of the k-th MRI template sub-image,
   $M_{patient}^{i}$ represents the MRI sub-image i,
   $M_{template}^{ik}$ represents the k-th MRI template sub-image corresponding to the MRI sub-image i, and
   K represents a number of the plurality of MRI template sub-image;

obtain the plurality of CT template sub-images corresponding to the plurality of MRI template sub-images from a CT template set in the MRI-CT atlas; and obtain the pseudo CT sub-image corresponding to the MRI sub-image according to the plurality of CT template sub-images and the matching relationship.

8. The device of claim 6, wherein the processor is caused by the machine-executable instructions to:

place the respective pseudo CT sub-images into border images for the attenuation units corresponding to the respective pseudo CT sub-images.

9. The device of claim 6, wherein the processor is caused by the machine-executable instructions to:

perform smoothing correction for respective adjacent borders of attenuation units in adjacent pseudo CT sub-images.

10. The device of claim 6, wherein the attenuation unit is an organ tissue of the subject.

* * * * *